United States Patent [19]
Shimizu

[11] Patent Number: 6,106,467
[45] Date of Patent: Aug. 22, 2000

[54] APPARATUS FOR ULTRASONIC DIAGNOSIS WITH VARIABLE FRAME RATE

[75] Inventor: Yutaka Shimizu, Kanagawa, Japan

[73] Assignee: Shimadzu Corporation, Kyoto, Japan

[21] Appl. No.: 09/192,061

[22] Filed: Nov. 13, 1998

[30]     Foreign Application Priority Data

Nov. 21, 1997 [JP]   Japan ................................ 9-320746

[51] Int. Cl.⁷ ..................................................... A61B 8/00
[52] U.S. Cl. ........................................... 600/443; 600/447
[58] Field of Search ..................................... 600/443, 444, 600/447, 440, 441, 442; 367/7, 11, 138, 140; 73/609, 610, 612, 632; 310/335

[56]               References Cited

U.S. PATENT DOCUMENTS

| | | | |
|---|---|---|---|
| 5,301,674 | 4/1994 | Erikson et al. | 600/447 |
| 5,318,033 | 6/1994 | Savord | 600/447 |
| 5,379,642 | 1/1995 | Reckwerrdt et al. | 600/447 |
| 5,797,846 | 8/1998 | Seyed-Bolorforosh et al. | 600/447 |
| 5,995,450 | 11/1999 | Cole et al. | 367/138 |

FOREIGN PATENT DOCUMENTS

| | | |
|---|---|---|
| 2-004351 | 1/1990 | Japan . |
| 2-004353 | 1/1990 | Japan . |
| 5-137716 | 6/1993 | Japan . |
| 7-275250 | 10/1995 | Japan . |

*Primary Examiner*—Marvin M. Lateef
*Assistant Examiner*—Ali M. Imam
*Attorney, Agent, or Firm*—Majestic, Parsons, Siebert & Hsue P.C.

[57]               ABSTRACT

An apparatus for ultrasonic diagnosis uses a probe to transmit ultrasonic waves to different focusing steps and to received reflected waves from target positions for diagnosis, controlled by a transmission-reception controller which also causes sectional images to be sequentially displayed in frames on a monitor. A frame rate calculator calculates from a frame rate for forming images at each of focusing steps at a specified depth. A frame rate comparator compares the frame rate calculated by the frame rate calculator with a specified threshold value determined by the timing of display by the monitor. A focusing controller thereby serves to adjust the number of focusing steps at the specified depth according to the result of comparison by the frame rate comparator such that an optimum number of focusing steps can be selected to obtain a dependably real-time clear images can be displayed.

6 Claims, 2 Drawing Sheets

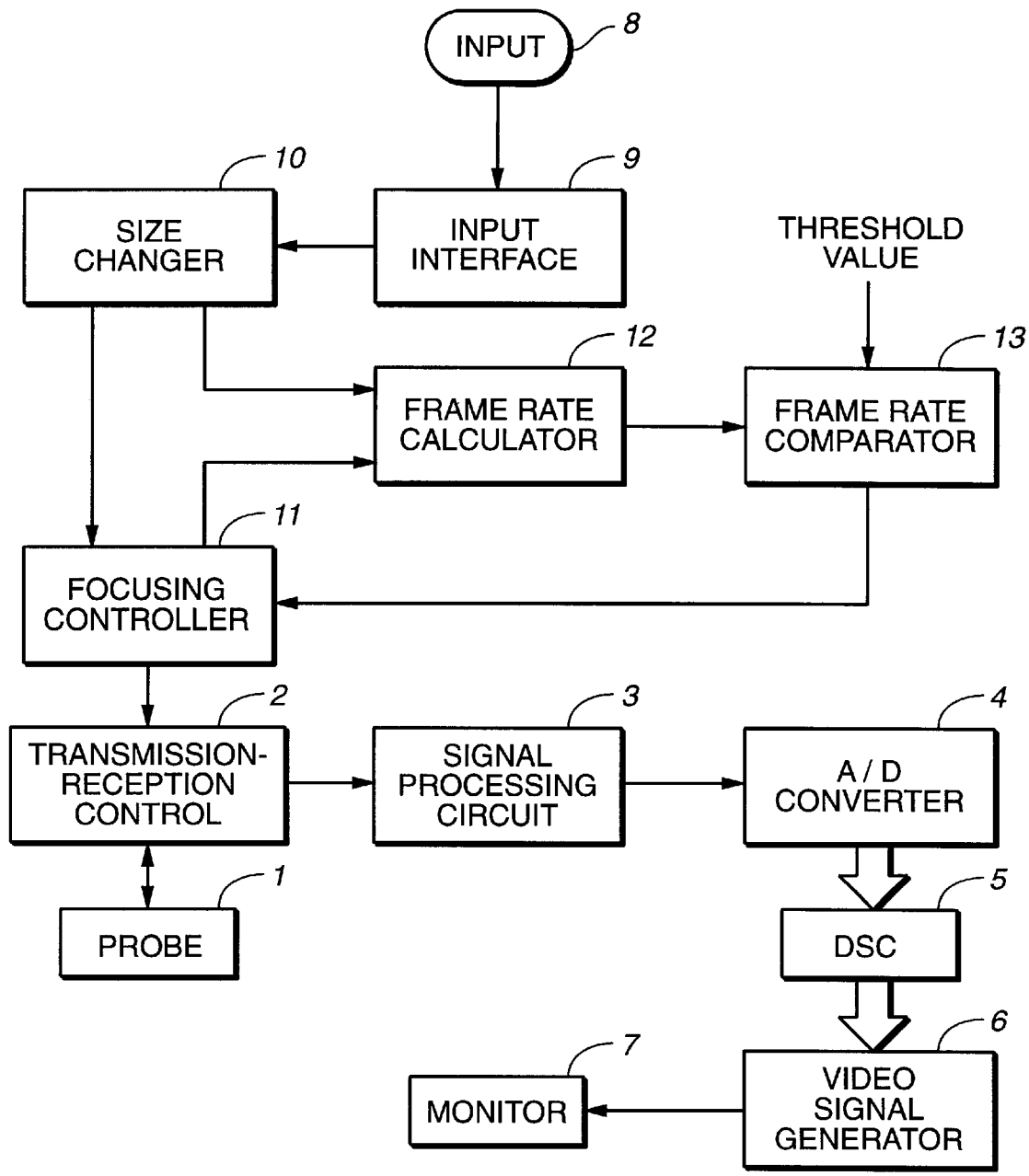
FIG._1

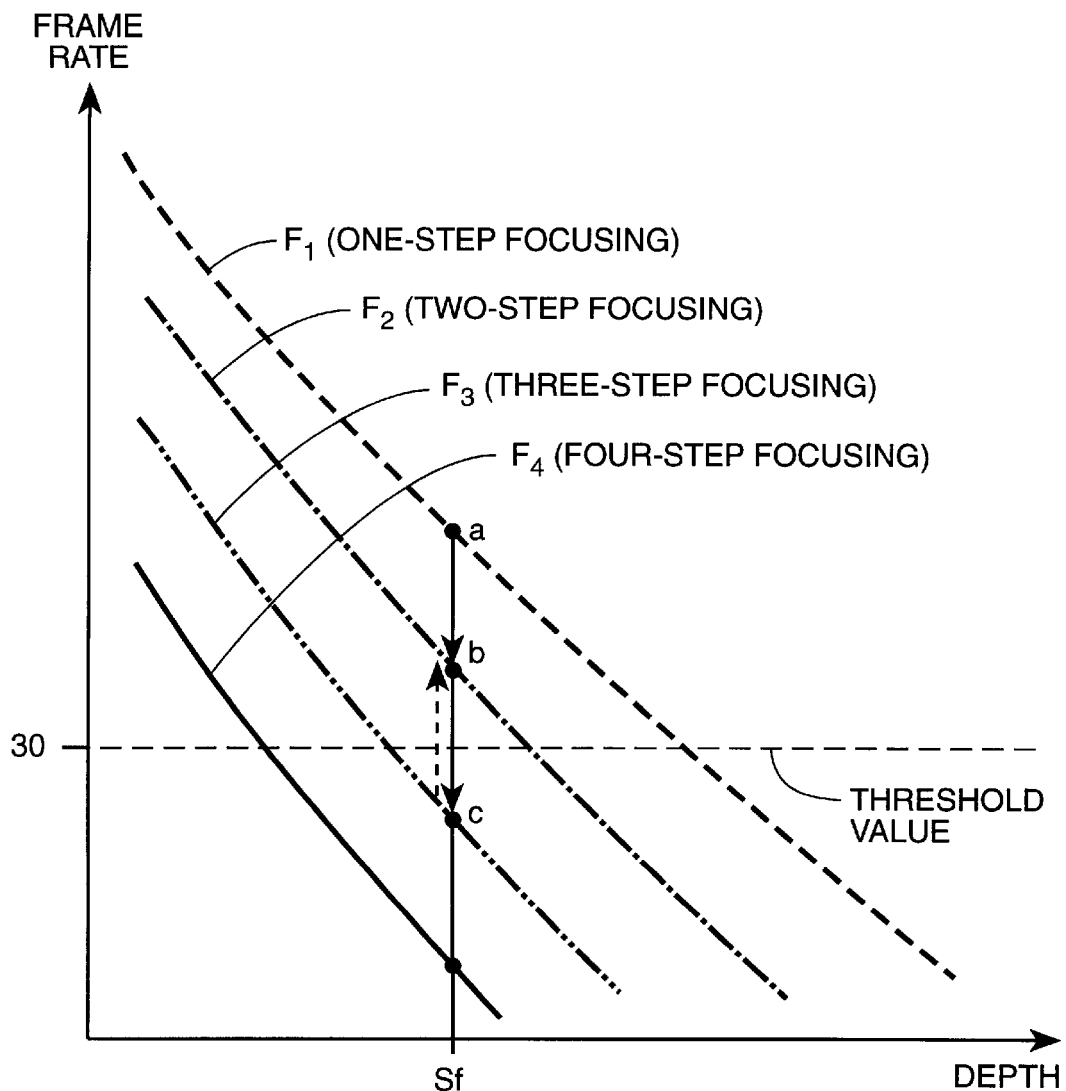
FIG._2

APPARATUS FOR ULTRASONIC DIAGNOSIS WITH VARIABLE FRAME RATE

BACKGROUND OF THE INVENTION

This invention relates to an apparatus for ultrasonic diagnosis and more particularly to the structure of its part for setting the number of focusing steps.

Most apparatus for ultrasonic diagnosis are capable of a so-called B-mode display, forming and displaying tomographic images on the basis of ultrasonic echoes. Such an apparatus is normally capable of changing the image size in several steps, allowing its operator to change the image size according to the depth of the target body part of a patient which is being diagnosed. Ultrasonic beams can thus be focused at the target positions of diagnosis, and the operator can obtain a tomographic image showing such target positions clearly.

Some of such apparatus for ultrasonic diagnosis adapted to make B-mode displays are also capable of increasing the number of focusing steps in the direction of the depth such that an image with improved azimuthal resolution at all levels of depth can be obtained by focusing the ultrasonic beams at every selectable level of the target body part. It is not the case, however, that a clear image can always be displayed under all circumstances by using such an apparatus and by switching the depth for disgnosis and the number of focusing steps.

If the depth of the target position is increased and the frame rate becomes less than the frame rate of a video output, for example 30 in NTSC system, such that the transmission and reception of ultrasonic waves and the formation of an image cannot be carried out at the timing for the display, the display of formed images may take place at a delayed timing, or some images may be skipped. In other words, a correct display may not be obtained in such a situation, and what the operator observes may not be what is actually taking place at the time of the observation.

If the number of focusing steps is increased, the azimuthal resolution improves all over the display screen and it becomes possible to obtain an image with improved overall clarity. On the other hand, however, since the frequency of wave transmission and reception in each direction increases, the frame rate decreases accordingly in such a case and it becomes impossible, as explained above, to capture the real-time movements of the target body part.

In view of the above, the prior art procedure has been to set the image size and the number of focusing steps appropriately, to observe the displayed image under these set conditions and then to adjust the image size and/or the number of focusing steps, depending on the condition of the observed displayed image. This means that the operator had to go through a series of cumbersome time-consuming operations before a reasonably clear and sufficiently accurate real-time image could be displayed. If the operator was not sufficiently skilled, furthermore, a satisfactorily accurate image could not be displayed at times.

SUMMARY OF THE INVENTION

It is therefore a general object of this invention to provide an improved apparatus for ultrasonic diagnosis capable of displaying a dependably real-time clear image.

A more specific object of this invention is to provide such an apparatus capable of automatically adjusting the number of focusing steps within an allowed limit dictated by the timing of the display once the image size is set.

An apparatus embodying this invention, with which the above and other objects can be accomplished, may be characterized not only as being capable of varying and adjusting the number of focusing steps in connection with ultrasonic wave transmission and reception but also as comprising a frame rate calculator, a frame rate comparator and a focusing controller. The frame rate calculator calculates a frame rate for forming images at each of focusing steps at a specified depth. The frame rate comparator compares the frame rate calculated by the frame rate calculator with a specified threshold value determined by the timing of display by a monitor for the apparatus. The focusing controller thereby serves to adjust the number of focusing steps at the specified depth according to the result of comparison by the frame rate comparator.

BRIEF DESCRIPTION OF THE DRAWINGS

The accompanying drawings, which are incorporated in and form a part of this specification, illustrate an embodiment of the invention and, together with the description, serve to explain the principles of the invention. In the drawings:

FIG. 1 is a schematic block diagram of an apparatus for ultrasonic diagnosis embodying this invention; and FIG. 2 is a graph of frame rate for explaining the operation of the apparatus of FIG. 1.

DETAILED DESCRIPTION OF THE INVENTION

The invention is described next by way of an example with reference to the drawings. In FIG. 1, numeral 1 indicates a probe which is controlled by a transmission-reception control circuit 2 to transmit and receive ultrasonic waves and is adapted to output echo signals according to ultrasonic waves received thereby. Each echo signal outputted by the probe 1 is transmitted through the transmission-reception control circuit 2 to a signal processing circuit 3 which serves to adjust its waveform and then to an analog-to-digital (A/D) convertor 4 which converts it into a digital echo data signal to be received by a digital scan convertor (DSC) 5. The function of the DSC 5 is to form from the echo data an image data signal for a sectional image and to transmit it to a video signal generator 6 for generating a video signal for a display according to the image data received from the DSC 5. A monitor 7 is adapted to receive this video signal from the video signal generator 6 and to thereby display a sectional image. Numeral 8 indicates an input section through which the operator can carry out various input operations such as switching the image size. Numeral 9 indicates an input interface, and numeral 10 indicates a size changer which is a component adapted to receive from the input section 8 through the input interface 9 an image size signal indicative of an image size and to output a size switching signal both to a focusing controller 11 and to a frame rate calculator 12.

The focusing controller 11 serves to control the transmission-reception control circuit 2 to thereby set the number of focusing steps and the focusing position. The action for increasing or decreasing the number of focusing steps is carried out in response to signals received from a frame rate comparator 13 (to be described below). The focusing controller 11 also serves to respond to the size switching signal from the size changer 10 by transmitting to the frame rate calculator 12 a signal indicative of the number of focusing steps which is currently set. The number of focusing steps is usually one at the beginning (or "the one-step focusing").

The frame rate calculator 12 is adapted to receive the size switching signal indicative of the depth of the target position from the size changer 10 and a signal indicative of the number of focusing steps from the focusing controller 11 and to calculate therefrom the speed at which an image for one frame is formed, or the current frame rate. The result of its calculation is outputted to the frame rate comparator 13 which serves to compare this calculated frame rate with a preliminarily inputted threshold value. This threshold value is determined according to the timing of display by the monitor 7. If the display at the monitor 7 is by the NTSC mode, for example, the threshold value is one which corresponds to the frame rate of 30.

The result of comparison made by the frame rate comparator 13 is transmitted to the focusing controller 11. The focusing controller 11 responds thereto by outputting to the transmission-reception control circuit 2 a signal for increasing or decreasing the number of focusing steps, as a result of which the number of focusing steps is increased or decreased.

The operations described above are explained next with reference to the graph shown in FIG. 2. This graph is for showing the relationship between the frame rate and the depth of the target position of diagnosis. As shown by the curves $F_1$, $F_2$, $F_3$, . . . in the graph, the frame rate generally decreases gradually as the depth of the target position increases and in a step-wise fashion as the number of focusing steps increases.

When a key in the input section 8 is operated as a command to change the image size, a corresponding signal is transmitted through the input interface 9 to the size changer 10 which, in turn, outputs a size switching signal to the focusing controller 11. In response, the focusing controller 11 serves to switch the image size but since the image size implies the depth of diagnosis, the depth of diagnosis is also switched as a result.

The size switching signal from the size changer 10 is received also by the frame rate calculator 12. The frame rate calculator 12 receives not only the size switching signal but also a signal from the focusing controller 11 indicative of the number of focusing steps at the time. On the basis of both these signals, the frame rate calculator 12 calculates the frame rate, or how fast an image corresponding to one frame is formed under the conditions of the newly set depth of position of diagnosis and the already set number of the focusing steps. Under the initial condition, there is only one focusing step, and the frame rate is calculated for the depth of that focusing step determined through the input section 8. The frame rate thus calculated is compared with the threshold value by the frame rate comparator 13, and it is thereby determined whether this calculated frame rate is within the region acceptable in view of the timing for display.

If the frame rate is higher than the threshold value, this means that the image is being formed with some time to spare, compared with the timing for display. In such a situation, the frame rate comparator 13 transmits a signal to the focusing controller 11 to inform the result of the comparison, causing the focusing controller 11 to increase the number of focusing steps by one. Under the initial condition in which the number of focusing steps was one, the number is increased to two. If the frame rate is lower than the threshold value, on the other hand, this means that the it takes a longer time to form an image than the timing for display. In such a situation, the frame rate comparator 13 similarly transmits a signal to the focusing controller 11 but it is so as to cause the focusing controller 11 to reduce the number of focusing steps by one.

When the focusing controller 11 thus causes the number of focusing steps to increase of decrease by one, a signal indicative of this change is inputted to the frame rate calculator 12. The frame rate calculator 12 responds thereto by adjusting the number of focusing steps by one (that is, either +1 or −1), and calculates the frame rate over again.

This process is explained next with reference to FIG. 2. Let letter "a" indicate the frame rate calculated initially by the frame rate calculator 12 at a position of diagnosis at depth $S_f$ set through the input section 8, (the number of focusing steps being one initially, as stated above.) Since this calculated frame rate "a" on the one-step focusing curve $F_1$ is higher than the threshold value, the focusing controller 11 increases the number of focusing steps by one (to two), and the frame rate calculator 12 calculates a new frame rate (indicated by letter "b") at the same set depth $S_f$ by using the two-step focusing curve $F_2$. If the frame rate "b" thus calculated is still higher than the threshold value, as shown in FIG. 2, the number of focusing steps is still further increased by one, and the frame rate calculator 12 calculates still another frame rate "c" at the same depth $S_f$ by using the three-step focusing curve $F_3$.

Calculation of frame rate, comparison with the threshold value and changing of the number of focusing steps are thus repeated until the calculated frame rate changes from higher to lower than the threshold value. When this finally happens (at "c" in the example described above with reference to FIG. 2), the number of focusing steps is set to the number in the previous cycle (2 in the example above) and is no longer changed thereafter. If the frame rate was lower than the threshold value to start with, on the other hand, the number of focusing steps is sequentially reduced each time by one, a frame rate is calculated by using the corresponding focusing curve for the same depth, and the number of focusing steps is fixed when the calculated frame rate first becomes higher than the threshold value (such as from "c" to "b"). In this manner, the number of focusing steps can be increased to the maximum within the limit of the timing for display. As a result, an image which is reliably on-time and clear as a whole can be obtained.

Although the invention was described above by way of an embodiment wherein the size changer 10, the frame rate calculator 12, the frame rate comparator 13 and the focusing controller 11 were each indicated as a block, these components may be formed as independent circuits, or alternatively, a central processing unit may be provided with a software program such that the functions of all these individual components are performed by such a central processing unit.

What is claimed is:

1. An apparatus for ultrasonic diagnosis for B-mode display and capable of transmitting and receiving waves to and from a variable number of focusing steps, said apparatus comprising:

a frame rate calculating means for calculating a frame rate at each number of focusing steps at a specified depth, said frame rate being indicative of the speed at which images for one frame are formed per unit time by said apparatus;

a frame rate comparator for comparing a frame rate calculated by said frame rate calculating means with a preliminarily inputted specified threshold value; and a focusing controller for adjusting the number of focusing steps at said specified depth according to the result of comparison by said frame rate comparator.

2. The apparatus of claim 1 wherein said frame rate calculating means calculates selectively either an initial frame rate or a frame rate corresponding to a previously set number of focusing steps, in accordance with said set specified depth, and wherein said focusing controller increases or decreases the number of focusing steps, depending on the result of comparison by said frame rate comparator.

3. The apparatus of claim 2 wherein said focusing controller sequentially increases by one the number of focusing steps as long as said frame rate comparator determines that the frame rate calculated by said frame rate calculating means is greater than said specified threshold value and sequentially decreases by one the number of focusing steps as long as said frame rate comparator determines that the frame rate calculated by said frame rate calculating means if less than said specified threshold value.

4. An apparatus for ultrasonic diagnosis comprising:
- a probe for transmitting and receiving ultrasonic wave signals;
- a transmission-reception control means for controlling said probe;
- an input means for allowing a user to specify input data therethrough;
- a size changer for outputting an image size signal indicative of the input data inputted through said input means;
- a monitor for displaying images;
- signal processing and video signal generating means for receiving image data from said transmission-reception control means and causing images to be displayed on said monitor sequentially in frames at a fixed frame rate;
- a frame rate calculating means for calculating a frame rate at each number of focusing steps at a specified depth according to said image size signal received from said size changer, said frame rate being indicative of the speed at which images for one frame are formed per unit time;
- a frame rate comparator for comparing a frame rate calculated by said frame rate calculating means with a preliminarily inputted threshold value determined according to said fixed frame rate; and
- a focusing controller for adjusting the number of focusing steps at said specified depth according to the result of comparison by said frame rate comparator and controlling said transmission-reception control means accordingly.

5. The apparatus of claim 4 wherein said frame rate calculating means calculates selectively either an initial frame rate or a frame rate corresponding to a previously set number of focusing steps, in accordance with said set specified depth, and wherein said focusing controller increases or decreases the number of focusing steps, depending on the result of comparison by said frame rate comparator.

6. The apparatus of claim 5 wherein said focusing controller sequentially increases by one the number of focusing steps as long as said frame rate comparator determines that the frame rate calculated by said frame rate calculating means is greater than said specified threshold value and sequentially decreases by one the number of focusing steps as long as said frame rate comparator determines that the frame rate calculated by said frame rate calculating means if less than said specified threshold value.

* * * * *